United States Patent [19]

Yoshikawa et al.

[11] Patent Number: 5,077,436
[45] Date of Patent: Dec. 31, 1991

[54] BIS(3-AMINOPHENOXY) AROMATICS AND METHOD OF PREPARING THE SAME

[75] Inventors: Yukihiro Yoshikawa, Zushi; Keizaburo Yamaguchi, Kawasaki; Kenichi Sugimoto; Yoshimitsu Tanabe, both of Yokohama; Akihiro Yamaguchi, Kamakura, all of Japan

[73] Assignee: Mitsui Toatsu Chemicals, Inc., Tokyo, Japan

[21] Appl. No.: 831,547

[22] Filed: Feb. 21, 1986

[30] Foreign Application Priority Data

| Feb. 22, 1985 | [JP] | Japan | 60-32568 |
| May 28, 1985 | [JP] | Japan | 60-113237 |
| Jun. 28, 1985 | [JP] | Japan | 60-140408 |
| Aug. 22, 1985 | [JP] | Japan | 60-183039 |
| Sep. 17, 1985 | [JP] | Japan | 60-203357 |
| Sep. 25, 1985 | [JP] | Japan | 60-210266 |
| Dec. 24, 1985 | [JP] | Japan | 60-289334 |

[51] Int. Cl.$^5$ .............................. C07C 209/36
[52] U.S. Cl. .................... 564/329; 564/321; 564/305; 564/315; 564/330; 564/415; 564/417; 564/418; 564/420; 564/421; 564/422; 564/423
[58] Field of Search ............... 564/321, 330, 441, 305, 564/315, 329, 415, 417, 418, 420, 421, 422, 423

[56] References Cited

U.S. PATENT DOCUMENTS

| 3,294,838 | 12/1966 | Morrison | 564/314 X |
| 3,895,064 | 7/1975 | Brode et al. | 564/430 X |
| 4,196,144 | 4/1980 | Darms | 564/430 |
| 4,314,086 | 2/1982 | Soula et al. | 568/584 X |
| 4,506,100 | 3/1985 | Schoenberg et al. | 564/430 |
| 4,521,623 | 6/1985 | Jones et al. | 564/430 |
| 4,526,608 | 7/1986 | Lee | 564/430 X |
| 4,650,905 | 3/1987 | Parg et al. | 564/430 X |

FOREIGN PATENT DOCUMENTS

| 3300585 | 7/1984 | Fed. Rep. of Germany | 564/430 |
| 7811824 | 4/1978 | France . | |
| 7911100 | 5/1979 | France . | |
| 54-39030 | 3/1979 | Japan . | |
| 5737580 | 8/1982 | Japan . | |
| 58-34464 | 7/1983 | Japan . | |

OTHER PUBLICATIONS

J. Schramm et al., Liebigs Ann. Chem., 740, 169-170 (1970).
H. M. Relles et al., J. Polymer Sci., Polym. Chem. Ed., 15, 2441-2451 (1977).
T. Takekoshi et al., J. Polymer Sci., Polym. Chem. Ed., 18, 3081-3088 (1980).
J. R. Beck et al., J. Org. Chem., 39 1839-1841 (1974).
T. Takekoshi et al., J. Polymer Sci., Polym. Chem. Ed., 18, 3081-3088 (1980).
J. R. Beck, Tetrahedron, 34, 2057-2068 (1978).
N. Kornblum et al., J. Org. Chem., 41, 1560-1564 (1976).
F. Montanari et al., Chem & Ind., 19 Jun. 412 (1982).
J. J. Randall et al., J. Org. Chem. 27, 4098-4101 (1962).
Chemical Abstracts, vol. 1, 210724u (1984), p. 613.

Primary Examiner—Richard L. Raymond
Attorney, Agent, or Firm—Fisher, Christen & Sabol

[57] ABSTRACT

Bis(3-nitrophenoxy) derivatives of aromatic or bridged aromatic hydrocarbons are derived from m-dinitrobenzene and dihydroxy derivatives of said hydrocarbons and certain substituted derivatives thereof by a condensation reaction in dipolar aprotic solvents in the presence of bases. The bis(3-nitrophenoxy) derivatives and derivatives obtained are successively reduced to afford bis-(3-aminophenoxy)derivatives. This is a new method for reacting the dihydroxy-derivatives with m-dinitrobenzene, and hence can prepare novel bis(3-aminophenoxy) derivatives such as 4,4'-bis(3-amino-phenoxy)biphenyl, 1-[4-(3-aminophenoxy)phenyl]-1,3,3-trimethyl-6-(3-aminophenoxy)indan, 6,6'-bis(3-aminophenoxy)3,3,3',3'-tetramethyl-1,1'spirobiindan, and methyl substituted 2,2'-bis[4-(3-aminophenoxy)phenyl]-propane.

15 Claims, No Drawings

BIS(3-AMINOPHENOXY) AROMATICS AND METHOD OF PREPARING THE SAME

BACKGROUND OF THE INVENTION

1. Field of the Invention

The present invention relates to bis(3-aminophenoxy) derivatives of aromatic or bridged aromatic hydrocarbons including substituted variants thereof (hereinafter abbreviated as bis(3-aminophenoxy)-derivatives) and the method for preparing the same which comprises conducting a condensation reaction of m-dinitrobenzene with dihydroxy-derivatives of aromatic or bridged aromatic hydrocarbons (hereinafter abbreviated as dihydroxy-derivatives) in dipolar aprotic solvents in the presence of bases, and successively reducing bis(3-nitrophenoxy) derivatives of aromatic or bridged aromatic hydrocarbons (hereinafter abbreviated as bis(3-nitrophenoxy)-derivatives) obtained thereby.

2. Description of the Prior Art

Regarding bis(3-aminophenoxy)-derivatives represented by the following general formula:

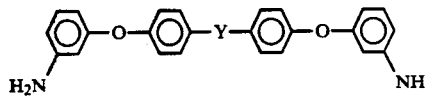

where Y is hydrocarbons of $C_1$-$C_{10}$, $-C(CF_3)_2-$, $-CO-$, $-S-$, $-SO-$, $-SO_2-$, or $-O-$, and having amino groups at the meta positions of ether linkage, 4,4'-bis(3-aminophenoxy)diphenylsulfone where Y is $-SO_2-$ in the general formula above mentioned is known to be prepared by the condensation of m-aminophenol with 4,4'-dichlorodiphenylsulfone in dimethylsulfoxide in the presence of potassium hydroxide (J. Schramm et al., Liebigs Ann. Chem., 740, 169 (1970), TOKKOSHO 58-35990). Preparing methods, however, have not yet concretely been known on the compounds having the divalent group where Y is $-C(CF_3)_2-$, $-C(CH_3)_2-$, $-CO-$, $-S-$, $-SO_2-$, or $-O-$.

SUMMARY OF THE INVENTION

The object of the present invention is to provide a novel method for cheaply and industrially preparing bis(3-aminophenoxy)-derivatives and to provide useful and novel bis(3-aminophenoxy)-derivatives for the materials of high-temperature stable polymers.

A hard research effort was conducted by the inventors of this invention to achieve above object. Unexpectedly, a new fact was found that bis(3-aminophenoxy)-derivatives could easily be derived from m-dinitrobenzene by the condensation with dihdroxy-derivatives. The method for preparing bis(3-aminophenoxy)-derivatives desired has been achieved by reducing the nitro compounds. Novel bis(3-aminophenoxy)-derivatives which had never been prepared could be provided by the new method.

The present invention is a method for preparing a bis(3-aminophenoxy)-derivative represented by the following general formulas:

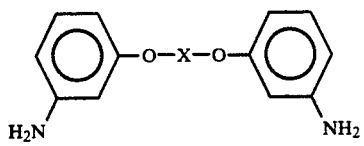

where X is

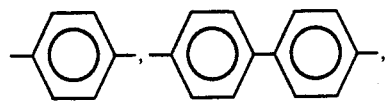

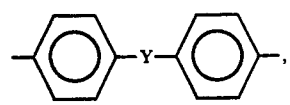

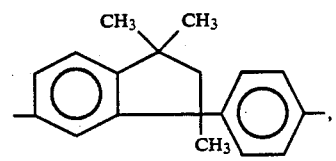

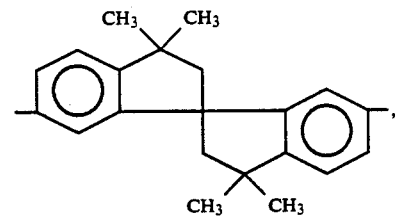

or

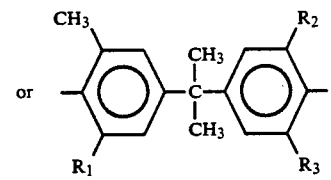

where
Y is hydrocarbons of $C_1$-$C_{10}$, $-C(CF_3)_2-$, $-CO-$, $-S-$, $-SO-$, $-SO_2-$, or $-O-$,
and $R_1$, $R_2$, $R_3$ are H, or $CH_3$,
which comprises conducting a condensation reaction of m-nitrobenzene in a dipolar aprotic solvent in the presence of a base with a dihydroxy-derivative represented by the following general formula:

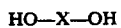

where X is the same as above, and reducing the resultant bis(3-aminophenoxy)-derivative represented by the general following formula:

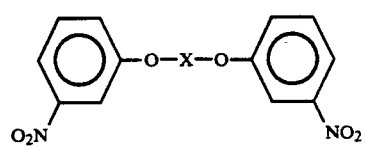

where X is the same as above.

Many examples are known on the substitution reaction of aromatic nitro compounds, activated by o- or p-located electron-withdrawing groups, with alcohols and phenols. (H. M. Relles et al., J. Polym. Sci., Polym. Chem. Ed., 15, 2441 (1977); J. R. Beck et al., J. Org. Chem., 39, 1839 (1974); T. Takekoshi et al., J. Polym. Sci., Polym. Chem. Ed., 18, 3069 (1980); J. R. Beck, Tetrahedron, 34, 2057 (1978).

Only a few examples, however, are known on the substitution reaction of inactive nitro compounds such as m-dinitrobenzene with alcohols, and only one example is found on the reaction with phenols.

For example:

(1) m-Nitroanisole was prepared by reacting m-dinitrobenzene with sodium methoxide at 25° C. for 16 hours in hexamethylphosphotriamide solvent (N. Kornblum et al., J. Org. Chem., 41, 1560 (1976)).

(2) m-Nitrophenyl alkyl ether was prepared by reacting m-dinitrobenzene with alkali metal alkoxide in the dipolar aprotic solvents in the presence of macro-cyclic polyethers (Toyota et al., TOKKAISHO 54-39030).

(3) m-Nitroanisol was prepared by reacting m-dinitrobenzene with sodium methoxide in chlorobenzene in the presence of phase-transfer catalysts (F. Montanari et al., Chem. & Ind., (1982), 412).

(4) The possibility of preparing 3-nitrodiphenylethers by reacting m-dinitrobenzene with alkali metal phenolates in polar solvents in the presence of macro-cyclic polyethers is described without detail (TOKKAISHO 54-39030)

In these methods, however, special solvents such as hexamethylphosphotriamide or special reagents such as expensive and toxic crown ethers are required for accelerating the reaction. Hence the substitution reaction of m-dinitrobenzene with phenols was assumed to be considerably difficult, and no examples have so far been found on the reaction under normal conditions of industry.

According to the method of this invention, a variety of bis-(3-aminophenoxy)-derivatives are prepared by performing the condensation reaction of m-dinitrobenzene with dihydroxy-derivatives which have so far been supposed difficult.

Therefore, the method of the present invention is very excellent in industrial application.

DETAILED DESCRIPTION OF THE INVENTION

The dihydroxy-derivatives in use for the present invention are represented by the following general formula:

HO—X—OH where X is

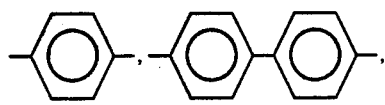

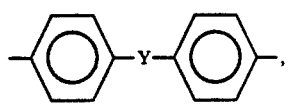

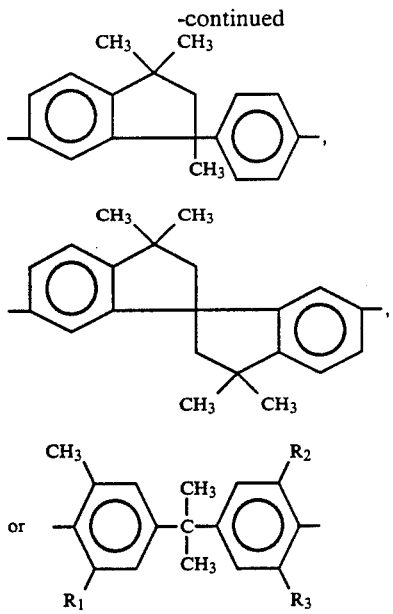

where
Y is hydrocarbons of $C_1$-$C_{10}$, —C(CF$_3$)$_2$—, —CO—, —S—, —SO—, —SO$_2$—, or —O—,
and $R_1$, $R_2$, $R_3$ and H, or CH$_3$.

Specifically, the dihydroxy-derivatives represented by the following general formula:

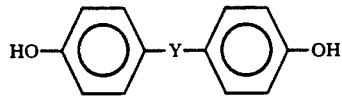

where Y is hydrocarbons of $C_1$-$C_{10}$, —C(CF$_3$)$_2$—, —CO—, —S—, —SO—, —SO$_2$—, or —O—, include, for example, 4,4'-dihydroxydiphenylmethane, 2,2-bis(4-hydroxyphenyl)propane, 2,4-bis(4-hydroxyphenyl)-2-methylpentane, 2,4-bis(4-hydroxyphenyl)-4-methyl-1-pentene, 2,2-bis(4-hydroxyphenyl)1,1,1,3,3,3-hexafluoropropane, 4,4'-dihydroxybenzophenone, 4,4'-dihydroxydiphenylsuflide, 4,4'-dihydroxydiphenylsulfoxide, 4,4'-dihydroxydiphenylsulfone and 4,4'-dihydroxydiphenylether.

The examples of dihydroxy-derivatives also include hydroquinone, 4,4'-dihydroxybiphenyl, 1-(4-hydroxyphenyl)-1,3,3-tri-methyl-6-hydroxyindan, 6,6'-dihydroxy-3,3,3',3'-tetramethyl-1,1'-spirobiindan and further include 2,2-bis(4-hydroxyphenyl)propane derivatives represented by the following general formula:

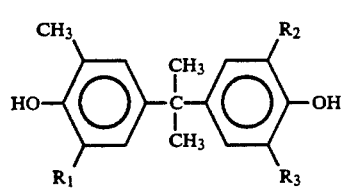

where $R_1$, $R_2$, and $R_3$ are H, or CH$_3$, such as 2-(4-hydroxy-3-methylphenyl)-2-(4'-hydroxyphenyl)propane, 2-(4-hydroxy-3,5-dimethylphenyl)-2-(4'-hydroxyphenyl)propane, 2,2-bis-(4-hydroxy-3-methylphenyl)-propane and 2,2-bis(4-hydroxy-3,5-dimethylphenyl)-propane.

Bis(3-aminophenoxy)-derivatives obtained in the method of this invention are represented by the following general formula:

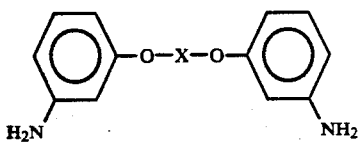

where X is the same as above, and include, for example, 4,4′-bis(3-aminophenoxy)diphenylmethane, 2,2-bis[4-(3-aminophenoxy)phenyl]propane, 2,4-bis[4-(3-aminophenoxy)-phenyl]-2-methylpentane, 2,4-bis[4-(3-aminophenoxy)phenyl]-4-methylpentene, 2,2-bis[4-(3-aminophenoxy)phenyl]-1,1,1,3,3,3-hexafluoropropane, 4,4′-bis(3-aminophenoxy)benzophenone, 4,4′-bis(3-aminophenoxy)diphenylsulfide, 4,4′-bis(3-aminophenoxy)diphenylsulfoxide, 4,4′-bis(3-aminophenoxy)diphenylsulfone and 4,4′-bis(3-aminophenoxy)-diphenylether.

Other bis(3-aminophenoxy)-derivatives include, for example, 1,4-bis(3-aminophenoxy)benzene, 4,4′-bis(3-aminophenoxy)biphenyl, 1-[4-(3-aminophenoxy)-phenyl]-1,3,3-trimethyl-6-(3-aminophenoxy)indan and 6,6′-bis(3-aminophenoxy)-3,3,3′,3′-tetramethyl-1,1′-spirobiindan.

Still other bis(3-aminophenoxy)-derivatives are methyl substituted derivatives of 2,2-bis[4-(3-aminophenoxy)phenyl]propane represented by the following general formula:

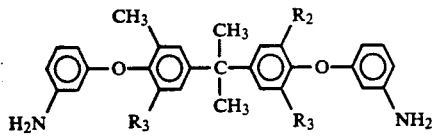

where $R_1R_2$, and $R_3$ and H, or $CH_3$, and include, for example, 2-[3-methyl-4-(3-aminophenoxy)phenyl]-2-[4-(3-aminophenoxy)phenyl]propane, 2-[3,5-dimethyl-4-(3-aminophenoxy)phenyl]-2-[4-(3-aminophenoxy)-phenyl]propane, 2,2-bis[3-methyl-4-(3-aminophenoxy)-phenyl]propane and 2,2-bis[3,5-dimethyl-4-(3-aminophenoxy)phenyl)]propane.

The above stated derivatives are new compounds except 1,4-bis(3-aminophenoxy)benzene.

In the method of this invention, the quantity in use of raw material such as dihydroxy-derivatives and m-dinitrobenzene is not limited, but normally m-dinitrobenzene is applied in the range of 1.5-4.0 times by mol of dihydroxy-derivatives.

The bases in use for the method of this invention are alkali metal oxide, hydroxide, carbonate, hydrogen carbonate, hydride or alkoxide, and include, for example, sodium oxide, lithium hydroxide, potassium carbonate, sodium carbonate, potassium hydrogen carbonate, sodium ethoxide, potassium tert-butoxide and potassium propoxide. Among these bases, alkali metal carbonate and hydrogen carbonate are preferably used. These bases may be used singly or in combination of two and more.

The quantity in use of these bases is normally in the range of 1-5 times by mol (1-10 equivalents), and preferably 1.5-3 times by mol of dihydroxy-derivatives.

Reaction accelerators which may be in use when needed in the method of this invention, include quaternary ammonium salts, quaternary phosphonium salts, nitrogen containing aliphatic polyethers, macro-cyclic polyethers such as crown ether, nitrogen containing macro-cyclic polyethers such as cryptate, phase-transfer catalysts such as polyethyleneglycol and its alkyl ethers, copper powder and copper salts. Among the reaction accelerators, nitrogen containing aliphatic polyethers represented by the following general formula:

$$N[-CH_2-CH_2-O(-CH_2-CH_2-O)_n-R]_3$$

where R is $C_1$-$C_4$ alkyl and n is an integer of 1 or 2, in particular, can still further accelerate the reaction in the method of the present invention.

The nitrogen containing aliphatic polyethers can be easily available (TOKKOSHO 57-37580, 58-34464). The polyethers of above general formula include, for example, tris(3-oxabutyl)amine, tris-(3,6-dioxaheptyl)amine, tris(3,6,9-trioxadecyl)amine, tris(3,6-dioxaoctyl)amine, tris(3,6,9-trioxadodecyl)amine, tris(3,6-dioxadecyl)amine, and tris(3,6,9-trioxatridecyl)amine. Tris(3,6-dioxaheptyl)amine is most frequently used for industrial application.

The quantity in use of these nitrogen containing aliphatic polyethers is unlimited. The catalytic amounts are normally sufficient and in the range of 0.1-10%, preferably 0.2-5% by mol of dihydroxy-derivatives. The effect on accelerating the reaction depends upon the quantity and performance of applied catalysts. When the catalysts are 1% by mol of dihydroxy-derivatives, reaction time can be reduced to a half to one tenth.

The solvents used in the process of this invention are the dipolar aprotic solvents and include, for example, N,N-dimethylformamide, N,N-dimethylacetamide, dimethylsulfoxide, dimethylsulfone, sulfolane, 1-methyl-2-pyrrolidinon, 1,3-dimethyl-2-imidazolidinon, N,N,N′,N′-tetramethylurea, hexamethylphosphotriamide, and 1,3-dimethyl-3,4,5,6-tetrahydro-2(H)pyrimidine. The quantity of solvents is not limited in particular and normally 1-15 times, preferably 3-10 times by weight of the raw materials.

On performing the reaction, procedures such as charging of the raw materials are not restricted. There are some procedures such as, for example:

(1) Specified quantity of bisphenol derivatives, bases and solvents are previously charged to form alkali phenolate of dihydroxy-derivatives before adding m-dinitrobenzene to carry out the reaction.

(2) All the raw materials containing m-dinitrobenzene are charged at the start and the reaction is performed as it is. Procedures are not restricted because any of them can conduct the reaction.

When alkali metal oxide or hydroxide is used as the bases, water generated in the reaction system can be removed, for example, gradually by introducing a nitrogen stream, or by azeotropic distillation with a small quantity of benzene, toluene, xylene, chlorobenzene and the like. When carbonate or hydrogen carbonate is used, no dehydration procedure is required in particular.

Reaction temperatures are normally in the range of 100-240° C. and preferably in the range of 120-180° C. Reaction time is normally 5-30 hours.

After ending the reaction, the reaction mixture is heated to distill off the solvents or as it is, and poured into water. Crude products thus obtained are used for the next reduction step as it is, or after purification when needed.

Reduction process applied for the next reducing reaction are not restricted in particular, applicable are conventional methods of reducing nitro groups to amino groups (for example, A New Experimental Chemistry Course, vol 15, Oxidation and Reduction (II), from Maruzen (1977)). Catalytic reduction or hydrazine reduction is preferred for the industrial application.

As to the catalysts in use for the catalytic reduction, applicable are conventional metal catalysts for reduction which include, for example, nickel, palladium, platinum, rhodium, ruthenium, cobalt and copper. Palladium catalyst is most preferred for industrial application. The catalysts can be used in a metallic state and normally applied by being supported on the carrier surface such as carbon, barium sulfate, silica gel, alumina and zeolite. Nickel, cobalt and copper are also used in the form of Raney catalyst.

The quantity in use of the catalysts is not limited in particular and is in the range of 0.01–10% by weight as metal of dihydroxy-derivatives. Normally, the range is 2–8% by weight when used in the state of metal and 0.1–5% by weight when supported on the carrier.

The solvents in use for the reaction are not limited in particular unless they are active in the reaction, and include, for example, alcohols such as methanol, ethanol and isopropylalcohol; glycols such as ethyleneglycol and propyleneglycol; ethers such as diethylether, dioxane, tetrahydrofuran and ethyleneglycol monomethylether; aliphatic hydrocarbons such as hexane and cyclohexane; aromatic hydrocarbons such as benzene, toluene and xylene; esters such as ethyl acetate and butyl acetate; halogenated hydrocarbons such as dichloromethane, chloroform, tetrachloromethane, 1,2-dichloroethane, 1,1,2-trichloroethane and tetrachloroethane; N,N-dimethyl formamide and dimethylsulfoxide. When water immiscible solvents are used and reaction speed is slow, the reaction can be accelerated by adding conventional phase-transfer catalysts such as quanternary ammonium salts or quanternary phosphonium salts. The quantity of solvent is not limited in particular and it is sufficient to suspend or dissolve the raw materials. The enough quantity of solvents is normally 0.5–10% times by weight of the raw materials.

The reaction temperatures are not limited in particular. The preferable range is generally 20–200° C. and particularly 20–100° C. The reaction pressure is normally about ambient to 50 kg/cm².

The reaction is normally conducted by dissolving or suspending the raw materials into the solvents before adding the catalysts, followed by introducing hydrogen to perform reduction at the specified temperatures under stirring. The end point of the reaction can be determined by the volume of hydrogen absorbed as well as by thin-layer chromatography or high speed liquid chromatography.

On the other hand, in the reduction with hydrazine, it is sufficient to use a small excess of hydrazine to the theoretical quantity. Preferably 1.2–2 times are used to perform the reduction.

Catalysts applied are above stated metal catalysts which are generally in use for the catalytic reduction. Industrially preferred are palladium/carbon, platinum/carbon and ferric chloride absorbed on active carbon. The quantity in use of the catalysts is not limited in particular, and normally in the range of 0.05–30% by weight as metal of bis(3-nitrophenoxy)-derivatives.

The solvents are the same as catalytic reduction. The reaction temperatures are not limited in particular and preferred range is generally 20–150° C. and particularly 40–100° C.

The reaction is normally conducted by dissolving or suspending the raw materials into the solvents before adding the catalysts, followed by dropping hydrazine to perform reduction at the specified temperatures under stirring. The end point of the reaction can be determined by thin-layer chromatography or high speed liquid chromatography.

After ending the reaction, the resulting mixture is hotfiltered to remove the catalysts, and the solvents are distilled off when needed. The desired bis(3-aminophenoxy)-derivatives are obtained as crude products which can be purified by recrystallization or by isolating in the form of hydrochloride.

EXAMPLES

The invention will be illustrated further with respect to the following Examples.

EXAMPLE 1

A 3 l glass reaction vessel was charged with 186 grams (1.0 mol) of 4,4'-dihydroxybiphenyl, 438 grams (2.6 mols) of m-dinitrobenzene, 363 grams of potassium carbonate and 2,000 ml of N,N-dimethylformamide. The mixture was reacted at 145–150° C. for 16 hours.

After the end of reaction, the resultant mixture was cooled and filtered to remove $KNO_2$. The filtrate was heated in a vacuum to distill off the solvent, cooled to 65° C., followed by adding 2,000 ml of methanol, and stirred for an hour. The separated crystals were filtered, washed with water and methanol successively, and dried to obtain 426 grams (99.5% yield) of 4,4'-bis(3-nitrophenoxy)biphenyl as brown crystals. The purity was 91.0% based on liquid chromatography.

A part of the crude crystals were recrystallized from dimethylsulfoxide to give the pure compound as light yellow crystals having a melting point of 134–136° C. Their analytical results were as follows.

| Elementary analysis ($C_{24}H_{16}N_2O_6$) | | | |
| --- | --- | --- | --- |
| | C | H | N |
| Calculated (%) | 67.3 | 3.74 | 6.54 |
| Found (%) | 67.34 | 3.70 | 6.48 |

MS: 428 (M+)

IR (KBr.cm$^{-1}$): 1520, 1350 (nitro group), 1240 (ether linkage)

In the next step, a 1 l glass reaction vessel was charged with 100 grams (0.23 mol) of crude 4,4'-bis(3-nitrophenoxy)biphenyl, 10 grams of active carbon, 1 gram of ferric chloride hexahydrate and 500 ml of ethyleneglycol monomethylether. The mixture was refluxed with stirring for 30 minutes, followed by dropwise adding 46 grams (0.92 mol) of hydrazine hydrate at 70°–80° C. during 3 hours. After ending the addition, the resulting mixture was stirred at 70°–80° C. for 5 hours to complete the reaction. The reaction product was cooled, filtered to remove the catalysts, and poured into 500 ml of water. The separated crystals were filtered, dissolved into a hot mixture of 48 grams of 35% hydrochloric acid and 540 ml of 50% aqueous iso-propylalcohol (IPA) solution, and allowed to cool. The separated 4,4'-bis(3-aminophenoxy)biphenyl hydrochloride was filtered, dissolved by warming into 540 ml of 50% aqueous IPA solution, and filtered again after adding 5 grams of active carbon.

The filtrate was neutralized with aqueous ammonia and separated crystals were filtered, washed with water and dried to obtain 72.0 grams (85% yield) of 4,4'-bis(3-aminophenoxy)biphenyl as colorless crystals having a melting point of 144°–146° C. The analytical results were as follows.

Purity: 99.6% (based on high speed liquid chromatography)

| Elementary analysis ($C_{24}H_{20}N_2O_2$) | | | |
| --- | --- | --- | --- |
|  | C | H | N |
| Calculated (%) | 78.26 | 5.43 | 7.61 |
| Found (%) | 78.56 | 5.21 | 7.66 |

MS: 368 (M+), 340, 184
IR (KBr.cm$^{-1}$): 3400 and 3310 (amino group), 1240 (ether linkage)

EXAMPLE 2

1 l sealed glass vessel was charged with 100 g (0.23 mol) of crude 4,4'-bis(3-nitrophenoxy)biphenyl obtained in Example 1, 1 g of 5% Pd/C (made by Japan Engelhardt Co.) and 350 ml of ethyleneglycol monoethylether. Hydrogen was introduced at 60°–65° C. with vigorous stirring. Absorption of hydrogen was stopped after 8 hours at the end of the reaction.

The same after-treatment and purification as Example 1 were conducted to obtain 70.3 grams (83% yield) of 4,4'-bis(3-aminophenoxy)biphenyl as colorless crystals having a melting point of 144°–146° C. and the purity of 99.3% based on high speed liquid chromatography.

EXAMPLE 3

The reaction procedure of Example 1 was repeated except 3.2 grams (0.01 mol) of tris(3,6-dioxaheptyl)amine was added and reacted for 2 hours at 145°–150° C.

The same after-treatment as Example 1 was conducted to obtain 426 grams (99.5% yield) of 4,4'-bis(3-nitrophenoxy)biphenyl as yellow brown crystals having the purity of 97.5% based on liquid chrommatography.

EXAMPLE 4

A 5 l glass reaction vessel was charged with 343 grams (1.5 mols) of 2,2-bis(4-hydroxyphenyl)propane, 605 grams (3.6 mols) of m-dinitrobenzene, 498 grams (3.6 mols) of potassium carbonate and 3.4 l of N,N-dimethylformamide. The mixture was reacted at 145°–150° C. for 10 hours, cooled after ending the reaction, and filtered to remove KNO$_2$. The filtrate was distilled in a vacuum to remove the solvent, cooled to 65° C., mixed with 1.8 l of methanol and stirred for an hour. The separated crystals were filtered, washed with water and methanol successively, and dried to obtain 600 grams (93.5% yield) of 2,2'-bis[4-(3-nitrophenoxy)phenyl]propane as yellow brown crystals, having the purity of 93% based on liquid chromatography.

A part of the crude crystals were recrystallized from ethyleneglycol monomethylether. Pure crystals were obtained as light yellow prisms having a melting point of 111°–113° C. and their analytical results were as follows.

| Elementary analysis ($C_{27}H_{22}N_2O_6$) | | | |
| --- | --- | --- | --- |
|  | C | H | N |
| Calculated (%) | 68.93 | 4.71 | 5.96 |
| Found (%) | 69.05 | 4.65 | 5.94 |

MS: 470 (Mhu +), 455 (M-CH$_3$)+
IR (KBr.cm$^{-1}$); 1520 and 1340 (nitro group)

In the second step, a 500 ml glass reaction vessel was charged with 100 grams (0.21 mol) of 2,2-bis[4-(3-nitrophenoxy)phenyl]propane, 10 grams of active carbon, 1 gram of ferric chloride hexa-hydrate and 300 ml of ethyleneglycol monomethylether. The mixture was refluxed with stirring for 30 minutes, followed by dropping 42 grams (0.84 mol) of hydrazine hydrate at 70°–80° C. during 2 hours, and stirred for further 5 hours at 70°–80° C. The resultant reaction mixture was cooled, filtered to remove the catalyst and 150 ml of ethyleneglycol monomethylether was distilled off. To the residual matter, 270 grams of 20% aqueous hydrogen chloride solution and 30 grams of sodium chloride were added, and cooled to 20°–25° C. with stirring. The separated crystals were filtered, dissolved into 30% aqueous IPA solution and neutralized with aqueous ammonia to separate crystals. The crystals were filtered, washed with water, dried and recrystallized from a mixture of benezene and n-hexane. Colorless crystals of 2,2-bis[4-(3-aminophenoxy)phenyl]propane thus obtained were 69.2 grams (75% yield) and had a melting point of 106°–108° C. and their analytical results were as follows.

Purity: 99.5% (based on high speed liquid chromatography)

| Elementary analysis ($C_{27}H_{26}N_2O_2$) | | | |
| --- | --- | --- | --- |
|  | C | H | N |
| Calculated (%) | 79.02 | 6.34 | 6.83 |
| Found (%) | 79.21 | 6.40 | 6.71 |

MS: 470 (M+), 455 (M-CH$_3$)+
IR (KBr.cm$^{-1}$): 3460 and 3370 (amino group) 1220 (ether linkage)

EXAMPLE 5

A 300 ml sealed glass vessel was charged with 50 grams (0.11 mol) of crude 2,2-bis[4-(3-nitrophenoxy)phenyl]propane prepared by the same method as Example 1, 2.5 grams of 5% Pd/C and 150 ml of ethyleneglycol monomethylether. Hydrogen was introduced at 60°–65° C. with vigorous stirring. The absorption of hydrogen was stopped after 8 hours at the end of reaction.

The after-treatment and purification of Example 4 were repeated to afford 36.6 grams (79% yield) of 2,2-bis[4-(3-aminophenoxy)phenyl]propane as colorless crystals having a melting point of 106°–108° C. and the purity of 99.6% based on high speed liquid chromatography.

EXAMPLE 6

The reaction procedure of Example 4 was repeated except 4.85 grams (0.015 mol) of tris(3,6-dioxaheptyl)amin was added and reacted at 150° C. for 4 hours.

The same after-treatments as Example 4 was conducted to afford 705.4 grams (99.8% yield) of 2,2-bis propane as yellow brown crystals having the purity of 98% based on liquid chromatography.

EXAMPLE 7

A 200 ml glass reaction vessel was charged with 20 grams (0.059 mol) of 2,2-bis(4-hydroxyphenyl)-1,1,1,3,3,3-hexafluoropropane, 24 grams (0.14 mol) of m-dinitrobenzene, 19.4 grams of potassium carbonate and 100 ml of N,N'-dimethylformamide. The mixture was reacted for 7 hours at 140-150° C. After ending the reaction, the resultant mixture was cooled and poured into 1,000 ml of water to separate crude 2,2-bis[b 4-(3-nitrophenoxy)phenyl]-1,1,1,3,3,3-hexafluoropropane as tarry matter. The tarry matter was dissolved into benzene and washed with water. The benzene layer was dehydrated with magnesium sulfate and applied for column chromatography to obtain 28.3 grams (83% yield) of pure 2,2-bis[4-(3-nitrophenoxy)phenyl]-1,1,1,3,3,3-hexafluoropropane as yellow oil.

The IR spectrum of this compound identified the desired product by the absence of hydroxyl absorption and by the presence of ether absorption.

IR (NaCl, neat, $cm^{-1}$): 1530 and 1350 (nitro group), 1240 (ether linkage)

In the next step, a 300 ml glass reaction vessel was charged with 20 grams (0.035 mol) of crude 2,2-bis[4-(3-nitrophenoxy)phenyl]-1,1,1,3,3,3-hexafluoropropane, 2 grams of active carbon, 0.2 gram of ferric chloride hexahydrate and 100 ml of IPA. The mixture was refluxed for 30 minutes with stirring and 7 grams (0.14 mol) of hydrazine hydrate was dropwise added at 60-70° C. during 2 hours, and refluxed for further 5 hours with stirring. The resultant reaction mixture was cooled, filtered to remove the catalyst and heated to distill off 60 ml of IPA. To the residue, 80 grams of 17.5% aqueous hydrochloric acid and 10 grams of sodium chloride were added and cooled to 20-25° C. with stirring. The separated crystals were filtered and recrystallized again from 40 ml of IPA and 80 grams of 17.5% aqueous hydrochloric acid. The resulting crystals were dissolved into 50% aqueous IPA solution and neutralized with aqueous ammonia to separate crystals. The crystals were filtered, washed with water, dried and recrystallized from the solvent mixture of benzene and n-hexane. Colorless crystals of 2,2-bis[4-(3-aminophenoxy)phenyl]-1,1,1,3,3,3-hexafluoropropane thus obtained were 13.6 grams (75% yield) and had a melting point of 137-139° C. The analytical results were as follows.

Purity: 99.2% (based on high speed liquid chromatography)

| Elementary analysis ($C_{27}H_{20}N_2F_6$) | | | |
| --- | --- | --- | --- |
| | C | H | N | F |
| Calculated (%) | 62.55 | 3.85 | 5.41 | 22.00 |
| Found (%) | 62.30 | 3.89 | 5.20 | 21.95 |

IR (KBr.$cm^{-1}$): 3480 and 3380 (amino group), 1240 (ether linkage)

EXAMPLE 8

A 500 ml glass reaction vessel was charged with 20 grams (0.093 mol) of 4,4'-dihydroxybenzophenone, 37.5 grams (0.22 mol) of m-dinitrobenzene, 30 grams of potassium carbonate and 350 ml of sulfolane. The mixture was reacted at 160-170° C. for 10 hours. After ending the reaction, the resultant mixture was poured into 2,000 ml of water and stirred for 30 minutes. The separated crystals were filtered, washed with water and dried to obtain 39 grams (92% yield) of 4,4'-bis(3-nitrophenoxy)benzophenone as brown crystals. A part of crude crystals was recrystallized from ethyleneglycol monomethylether to obtain the pure compound as light yellow crystals having a melting point of 189-191° C. The analytical results were as follows:

| Elementary analysis ($C_{25}H_{16}N_2O_7$) | | | |
| --- | --- | --- | --- |
| | C | H | N |
| Calculated (%) | 65.09 | 3.51 | 6.14 |
| Found (%) | 66.07 | 3.42 | 6.04 |

IR (KBr.$cm^{-1}$): 1650 (carbonyl group), 1250 and 1345 (nitro group), 1245 (ether linkage)

In the next step, a 300 ml glass reaction vessel was charged with 25 grams (0.06 mol) of crude 4,4'-bis(3-nitrophenoxy)benzophenone, 2.5 grams of active carbon, 0.25 gram of ferric chloride hexahydrate and 130 ml of ethyleneglycol monomethylether.

The mixture was stirred for 30 minutes at 70-80° C. and then 12 grams (0.24 mol) of hydrazine hydrate were dropwise added at 70-80° C. during 2 hours and stirred for further 6 hours at 70-80° C. The resultant reaction mixture was cooled, filtered to remove the catalyst, and the solvent was distilled off. The residue was dissolved by warming into the mixture of 13 grams of 35% hydrochloric acid and 60 ml of water, and 6 grams of sodium chloride were added, and cooled to separate the hydrochloride of the product. The hydrochloride was filtered, recrystallized again from 10% aqueous sodium chloride solution and dissolved by warming into 90 grams of 50% aqueous IPA solution. Then 1 gram of active carbon was added to the resulting hydrochloride solution which was filtered and neutralized with aqueous ammonia to separate crystals. The crystals were filtered, washed with water, dried to obtain 19.0 grams (80% yield) of 4,4'-bis(3-aminophenoxy)benzophenone as colorless crystals having a melting point of 142-144° C. The analytical results were as follows.

Purity: 99.3% (based on high speed liquid chromatography)

| Elementary analysis ($CH_{25}H_{20}N_2O_3$) | | | |
| --- | --- | --- | --- |
| | C | H | N |
| Calculated (%) | 75.76 | 5.05 | 7.07 |
| Found (%) | 75.60 | 5.20 | 6.99 |

MS: 396($M^+$), 212

IF(KBr.$cm^{-1}$): 3470 and 3370 (amino group, 1625 (carbonyl group), 1220 and 1240 (ether linkage)

EXAMPLE 9

A reaction vessel was charged with 20 grams (0.08 mol) of 4,4'-dihydroxydiphenylsulfone, 32.3 grams (0.19 mol) of m-dinitrobenzene, 26.1 grams of potassium carbonate and 150 ml of N,N-dimethylformamide. The mixture was reacted for 15 hours at 145-150° C. After ending the reaction, the resultant mixture was poured into 2,000 ml of water and stirred for 30 minutes. The separated crystals were filtered, washed with water, and dried to obtain 35.4 grams (90% yield) of 4,4'-bis(3-nitrophenoxy)diphenylsulfone as brown crystals. A part of crude crystals were recrystallized from benzene to obtain pure compound as light yellow crystals having a melting point of 149-150° C. The analytical results were as follows.

| Elementary analysis ($C_{24}H_{16}N_2O_8S$) | | | |
|---|---|---|---|
| | C | H | N | S |
| Calculated (%) | 58.54 | 3.25 | 5.7 | 6.5 |
| Found (%) | 58.69 | 3.12 | 5.6 | 6.6 |

IR (KBr.cm$^{-1}$): 1520 and 1355 (nitro group), 1340 and 1150 (sulfonyl group), 1240 (ether linkage)

In the next step, a 300 ml glass reaction vessel was charged with 25 grams (0.055 mol) of crude 4,4'-bis(3-nitrophenoxy)diphenylsulfone, 2.5 grams of active carbon, 0.25 gram of ferric chloride hexahydrate and 130 ml of ethyleneglycol monomethylether, and refluxed for 30 minutes with stirring. After dropping 11 grams (0.22 mol) of hydrazine hydrate at 70-80° C. during 2 hours, the mixture was stirred for further 6 hours at 70-80° C., followed by cooling and filtering to remove the catalyst. The solvent was distilled off in a vacuum and then 12 grams of 35% hydrochloric acid and 73 ml of water were added to the residue which was dissolved by warming. Hydrochloride was separated by cooling after addition of 7 grams of sodium chloride. The hydrochloride was filtered and recrystallized again from 10% aqueous sodium chloride solution and then dissolved into 100 ml of 50% aqueous IPA solution and filtered after adding 1 gram of active carbon. The filtrate was neutralized with aqueous ammonia to separate crystals which were filtered, washed with water and dried. By recrystallizing from ethanol, 18.8 grams (79% yield) of 4,4'-bis(3-aminophenoxy)diphenylsulfone was obtained as colorless crystals having a melting point of 134-136° C. The analytical results were as follows.

Purity: 99.2% (high speed liquid chromatography)

| Elementary analysis ($C_{24}H_{20}N_2O_4S$) | | | |
|---|---|---|---|
| | C | H | N | S |
| Calculated (%) | 66.67 | 4.63 | 6.48 | 7.41 |
| Found (%) | 66.68 | 4.66 | 6.41 | 7.56 |

IR (KBr.cm$^{-1}$): 3480 and 3380 (amino group), 1310 and 1150 (sulfonyl group), 1230 (ether linkage)

EXAMPLE 10

A reaction vessel was charged with 218 grams (1 mol) of 4,4'-dihydroxydiphenylsulfide, 403 grams (2.4 mols) of m-dinitrobenzene, 331 grams (2.4 mols) of potassium carbonate and 2.5 l of N,N-dimethylformamide. The mixture was reacted at 145-150° C. for 20 hours. After ending the reaction, the resultant mixture was cooled, filtered and distilled in a vacuum to remove the solvents. The residue was cooled to 65° C., charged with 800 ml of methanol and stirred for an hour. The separated crystals were filtered, washed with methanol and dried to obtain 429 grams (92.3% yield) of 4,4'-bis-(3-nitrophenoxy)diphenylsulfide. The crude crystals had the purity of 85% based on liquid chromatography, and recrystallized from ethyleneglycol monomethylether to obtain pure compound as light yellow crystals having a melting point of 97-99° C. (corr.).

| Elementary analysis ($C_{24}H_{16}N_2O_6S$) | | | |
|---|---|---|---|
| | C | H | N | S |
| Calculated (%) | 62.60 | 3.47 | 6.09 | 6.96 |
| Found (%) | 62.87 | 3.29 | 6.02 | 6.77 |

MS (FD): 460(M+)

IR (KBr.cm$^{-1}$): 1510 and 1345 (nitro group), 1230 (ether linkage)

In the next step, a reaction vessel was charged with 428 grams (0.93 mol) of crude product thus obtained, 22.6 grams of active carbon, 0.9 gram of ferric chloride hexahydrate and 1.5 l of ethyleneglycol monomethyl-ether and stirred under refluxing for 30 minutes, followed by dropping 155.2 grams (3.1 mols) of hydrazine monohydrate during 2 hours and further stirring for 3.5 hours under refluxing. The resultant mixture was cooled, filtered to remove the catalyst and concentrated in a vacuum. The residue was charged with 205 ml of 35% hydrochloric acid, 1,120 ml of water and 480 ml of IPA and was dissolved by warming, charged with 20 grams of active carbon, and hot-filtered.

After adding 112 grams of sodium chloride, the filtrate was cooled to separate hydrochloride crystals. The crystals were filtered, neutralized with aqueous ammonia and 265 grams (66% yield) of 4,4'-bis(3-aminophenoxy)diphenylsulfide was obtained as colorless crystals having a melting point of 112.4-113.4° C. (corr.). The analytical results are as follows.

Purity: 99.9% and more

| Elementary analysis ($C_{24}H_{20}N_2O_2S$) | | | |
|---|---|---|---|
| | C | H | N | S |
| Calculated (%) | 71.97 | 5.03 | 7.00 | 8.01 |
| Found (%) | 71.90 | 4.54 | 6.92 | 7.72 |

MS (FD): 400 (M+)

IR (KBr.cm$^{-1}$): 3390 and 3300 (amino group), 1220 (ether linkage)

EXAMPLE 11

The procedure of EXAMPLE 10 was repeated except 3.23 grams (0.01 mol) of tris(3,6-dioxaheptyl)amine was added and reacted for 5 hours 145-150° C.

The same after-treatment as Example 10 was performed and 453 grams (98.5% yield) of 4,4'-bis(3-nitrophenoxy)diphenylsulfide were obtained as yellow brown crystals. The purity was 95% based on liquid chromatography.

EXAMPLE 12

A reaction vessel was charged with 21 grams (0.125 mol) of m-dinitrobenzene, 5.5 grams (0.05 mol) of hydroquinone, 13.8 grams (0.1 mol) of anhydrous potassium carbonate and 100 ml of dimethylsulfoxide. The reaction was conducted at 130-135° C. for 7 hours with stirring under the ventilation of nitrogen.

After ending the reaction, the resultant mixture was poured into 300 ml of water to separate brown crystals. The crystals were filtered, dried, dissolved by warming into 100 ml of benzene, and hot-filtered to remove insoluble matter.

The filtrate was concentrated to separate light brown crystals. The crystals were filtered, washed with hot methanol, and dried to obtain 10.3 grams (58.5% yield) of 1,4-bis(3-nitrophenoxy) benzene, which was recrystallized from benzene to obtain pure product as light brown prisms having a melting point of 158–160° C.

| Elementary analysis ($C_{18}H_{12}N_2O_6$) | | | |
|---|---|---|---|
| | C | H | N |
| Calculated (%) | 61.37 | 3.43 | 7.95 |
| Found (%) | 61.74 | 3.39 | 8.03 |

In the next step, a reaction vessel was charged with 7 grams (0.02 mol) of 1,4-bis(3-nitrophenoxy)benzene above obtained, 0.1 gram of 5% Pd/C catalyst and 25 ml of IPA and introduced hydrogen gas with vigorous stirring. The reaction was carried out at 60–70° C. for 4 hours and hydrogen absorption was stopped at 2,700 ml. After the end of reaction, the resultant mixture was immediately hot-filtered at the same temperature and allowed to cool. 1,4-Bis-(3-aminophenoxy)benzene was separated as white needles which were filtered, washed and dried to obtain 5.35 grams (91.5% yield) of pure product having a melting point of 126–127° C.

| Elementary analysis ($C_{18}H_{16}N_2O_2$) | | | |
|---|---|---|---|
| | C | H | N |
| Calculated (%) | 73.95 | 5.52 | 9.58 |
| Found (%) | 73.9 | 5.55 | 9.61 |

EXAMPLE 13

A reaction vessel with a stirrer, thermometer, and reflux condenser was charged with 67.1 grams (0.25 mol) of 1-(4-hydroxyphenyl)-1,3,3-trimethyl-6-hydroxyindan, 100.9 grams (0.6 mol) of m-dinitrobenzene, 69.1 grams (0.5 mol) of anhydrous potassium carbonate and 650 ml of N,N-dimethylformamide. The reaction was carried out at 150–153° C. for 7 hours with stirring under ventilation of nitrogen.

After the end of reaction, the resultant mixture was filtered to remove inorganic salt and concentrated in a vacuum with a evaporator. The brown oily residue thus obtained was mixed with 280 ml of ethyleneglycol monomethylether and 20 ml of water, dissolved by warming, and allowed to cool. The separated crystals were filtered, washed and dried to obtain 112.5 grams (88.1% yield) of 1-[4-(3-nitrophenoxy)phenyl]-1,3,3-trimethyl-6-(3-nitrophenoxy)indan. By recrystallizing from ethanol, pure product was obtained as light yellow needles having a melting point of 90–92° C.

| Elementary analysis ($C_{30}H_{26}N_2O_6$) | | | |
|---|---|---|---|
| | C | H | N |
| Calculated (%) | 70.58 | 5.13 | 5.49 |
| Found (%) | 70.62 | 5.18 | 5.43 |

In the next step, a sealed reduction vessel with a stirrer and thermometer was charged with 10.21 grams (0.02 mol) of 1-[4-(3-nitrophenoxy)phenyl]-1,3,3-trimethyl-6-(3-nitrophenoxy)indan above obtained, 0.3 gram of 5% Pd/C catalyst and 30 ml of ethanol, and hydrogen gas was introduced with vigorous stirring. The reaction was carried out at 62–68° C. for 4 hours and hydrogen absorption was stopped at 2,760 ml. After the end of reaction, the resulting mixture was filtered to remove the catalyst and concentrated in a evaporator to recover the solvent.

The concentrated residue was mixed with 6.5 grams of concentrated hydrochloric acid and 50 ml of 20% aqueous IPA solution, dissolved by warming, charged with active carbon and hot-filtered. The filtrate was dropped into dilute aqueous ammonia to separate precipitate which was filtered, washed and dried. 1-[4(3-aminophenoxy)phenyl]-1,3,3-trimethyl-6-(3-aminophenoxy)indan thus obtained was 8.5 grams (94.3% yield) and had a melting point of 70–72° C. The analytical results were as follows.

| Elementary analysis ($C_{30}H_{30}N_2O_2$) | | | |
|---|---|---|---|
| | C | H | N |
| Calculated (%) | 79.97 | 6.71 | 6.22 |
| Found (%) | 80.12 | 6.76 | 6.20 |

NMR Sepctrum: Solvent: Acetone - $D_6$, Temperature: room temperature. 1.05 ppm ( 3H singlet), 1.35 ppm ( 3H singlet), 1.65 ppm ( 3H singlet), 2.3–2.5 ppm ( 2H multiplet), 3.6–4.2 ppm ( 4H singlet), 6.0–7.3 ppm (15H multiplet)

MS Spectrum: (M/e) $M^+$ 450, 435, 312, 250, 218

EXAMPLE 14

An autoclave was charged with 12.8 grams of 1-[4-(3-nitrophenoxy)phenyl]-1,3,3-trimethyl-6-(3-nitrophenoxy)indan obtained in Example 13, 1 gram of Raney nickel catalyst and 50 ml of diethyleneglycol dimethylether. Reduction was carried out at 80–90° C. for an hour under the hydrogen pressure of 30 kg/cm$^2$. The after-treatment of Example 13 was repeated to obtain 9.3 grams (82.5% yield) of the desired product having a melting point of 70–72° C/

EXAMPLE 15

A reaction vessel with a stirrer, thermometer, and reflux condenser was charged with 77.1 grams (0.25 mol) of 6,6'-dihydroxy-3,3,3'3,'-tetramethyl-1,1'-spirobiindan, 100.9 grams (0.6 mol) of m-dinitrobenzene, 69.1 grams (0.5 mol) of anhydrous potassium carbonate and 650 ml of N,N-dimethylformamide. The reaction was conducted at 150–153° C. for 12 hours with stirring under ventilation of nitrogen. After the end of reaction, the resultant mixture was poured into 650 ml of water. The separated light brown precipitate was filtered, washed with IPA and dried. 6,6'-Bis(3-nitrophenoxy)-3,3,3'3,'-tetramethyl-1,1'-spirobiindan obtained was 116.5 grams (84.6% yield). Pure product was prepared by recrystallizing from ethylalcohol as light brown needles having a melting point of 173.5–175° C.

| Elementary analysis ($C_{33}H_{30}N_2O_6$) | | | |
|---|---|---|---|
| | C | H | N |
| Calculated (%) | 72.0 | 5.49 | 5.09 |
| Found (%) | 71.83 | 5.39 | 5.10 |

In the next step, a sealed reduction vessel with a stirrer and thermometer was charged with 11 grams (0.02 mol) of 6,6'-bis-(3-nitrophenoxy)-3,3,3'3'-tetramethyl-1,1'-spirobiindan, 0.3 g of 5% Pd/C catalyst and 40 ml of ethyleneglycol monomethylether, and introduced hydrogen gas under vigorous stirring.

The mixture was reacted at 70–80° C. for 8 hours and hydrogen absorption was stopped at 2,650 ml. After ending the reaction, the resultant mixture was hot-filtered to remove the catalyst and diluted with 50 ml IPA. The separated crystals were filtered, washed with IPA and dried.

6,6'-Bis(3-aminophenoxy)-3,3,3',3'-tetramethyl-1,1'-spirobiindan obtained as white needles was 7.5 grams (76.4% yield) and had a melting point of 205–206° C. The analytical results were as follows.

| Elementary analysis ($C_{33}H_{34}N_2O_2$) | | | |
|---|---|---|---|
| | C | H | N |
| Calculated (%) | 80.77 | 6.98 | 5.71 |
| Found (%) | 80.62 | 7.05 | 5.70 |

MMR Spectrum: Solvent: Acetone-$D_6$, Temperature: room temperature, 1.4 ppm (12H doublet), 2.2–2.5 ppm ( 4H multiplet), 6.0–6.5 ppm ( 8H multiplet), 6.5–7.3 ppm ( 6H multiplet)

MS Sepctrum: (M/e) M+490, 475, 238, 65

EXAMPLE 16

The procedure of Example 15 was repeated by using 80 grams (0.8 mol) of anhydrous polassium hydrogen carbonate in place of anhydrous potassium carbonate and 800 ml of 1,3-dimethyl-2-imidazolidinon in place of N, N-dimethylformamide. The reaction was conducted at 170–175° C. for 10 hours. The intermediate thus obtained, 6,6'-bis(3-nitrophenoxy)-3,3,3',3'-tetramethyl-1,1'-spirobiindan, was 112 grams (81.4% yield).

A reduction vessel was charged with 11 grams of the nitro compound obtained, 0.2 gram of 5% Pt/C catalyst and 100 ml of ethanol, and reduction was conducted by introducing hydrogen under vigorous stirring.

After the end of reaction, the resultant mixture was filtered to remove catalyst, concentrated, followed by dropping 75 grams of 15% aqueous hydrochloric acid. The separated hydrochloride of the desired product was filtered, washed with water and neutralized with stirring in dilute aqueous ammonia. The separated crystals were filtered, washed with water and dried to obtain 8.75 grams (89.2% yield) of the desired product having a melting point of 205–206° C.

EXAMPLE 17

A 1 l glass reaction vessel was charged with 71 grams (0.25 mol) of 2,2-bis (4-hydroxy-3,5-dimethylphenyl)-propane, 100.9 grams (0.6 mol) of m-dinitrobenzene, 82.8 grams of potassium carbonate and 660 ml of N,N-dimethylformamide. The mixture was reacted at 140–150° C. for 15 hours. After the end of reaction, the resultant mixture was cooled, filtered to remove potassium nitrite and the solvent was distilled from the filtrate. The residue was cooled to 90° C., charged with 700 ml of water and stirred for an hour. Separated crystals were filtered, washed with water to obtain crude 2,2'-bis[3,5-dimethyle-4-(3-nitrophenoxy)phenyl]propane as brown crystals.

In the next step, a 1 l glass reaction vessel was charged with brown crystals above obtained, 13 grams of active carbon, 1.3 grams of ferric chloride hexahydrate and 550 ml of ethyleneglycol monomethylether, and refluxed for 30 minutes with stirring. Then 50 grams (1.0 mol) of hydrazine hydrate was dropped at 70–80° C. during 2 hours and stirring was continued for further 7 hours at 70–80° C. The reaction mixture was cooled, filtered to remove the catalyst and ethyleneglycol monomethylether was distilled off. The residue was added with 250 grams of 30% aqueous hydrochloric acid, 120 ml of methanol and further 30 grams of sodium chloride successively and cooled to 20–25° C. with stirring. The separated crystals were filtered, dissolved into 560 ml of 50% aqueous methanol solution, added with 50 grams of sodium chloride and cooled with stirring to 20–25° C. The separated crystals were filtered, neutralized in water with ammonia, and filtered, washed with water and dried. By recrystallizing from a solvent mixture of toluene and n-heptane, 88.5 grams (76% yield) of 2,2-bis[3,5-dimethyl-4-(3-aminophenoxy)phenyl]propane were obtained as pale brown crystals having a melting point of 112–114° C. The analytical results are as follows.

Purity: 99.5% (based on high sped liquid chromatography)

| Elementary analysis ($C_{31}H_{34}N_2O_2$) | | | |
|---|---|---|---|
| | C | H | N |
| Calculated (%) | 79.83 | 7.30 | 6.01 |
| Found (%) | 80.15 | 6.90 | 5.85 |

IR(KBr.$cm^{-1}$): 1120 (ether linkage), 3440 and 3350 (ammonium group)

EXAMPLE 18

A 1 l glass reaction vessel was charged with 64 grams (0.25 mol) of 2,2-bis (4-hydroxy-3-methylphenyl)propane, 100.9 grams (0.6 mol) of m-dinitrobenzene, 82.8 grams of potassium carbonate and 650 ml of N,N-dimethylformamide. The mixture was reacted at 145–150° C. for 8 hours, cooled after ending the reaction and poured into 3 l of water. 2,2-Bis[3-methyl-4-(3-nitrophenoxy)-phenyl]propane was separated as tarry matter. The tarry matter was washed with water.

In the next step, a 1 l glass reaction vessel was charged with above obtained tarry matter, 12 grams of active carbon, 1.2 grams of ferric chloride hexahydrate and 630 ml of ethyleneglycol monomethylether, and refluxed for 30 minutes with stirring. The mixture was dropped with 50 grams (1.0 mol) of hydrazine hydrate at 70–80° C. during 2 hours and stirred for 6 hours under refluxing. After ending the reaction, the resulting mixture was cooled, filtered to remove the catalyst and ethyleneglycol monomethylether was distilled off. The residue was mixed with 500 ml of 20% aqueous methanol solution and 62.5 grams of concentrated hydrochloric acid, dissolved by warming, followed by adding 60 grams of sodium chloride, and cooled to 20–25° C. The separated crystals were filtered, dissolved again by warming in 450 ml of 20% aqueous methanol solution, followed by adding 45 grams of sodium chloride, and cooled with stirring to 20–25° C. The separated crystals were filtered, neutralized in water with aqueous ammonia, filtered again and washed with water. The crystals thus obtained was dissolved by warming in toluene. Separated water layer was removed. Crystals were separated by adding n-heptance to the solution, was filtered and dried to obtain 79.5 grams (72.6% yield) of 2.2-bis[3-methyl-4-(3-aminophenoxy)phenyl]-propane as pale brown crystals having a melting point of 146–148° C. The analytical results were as follows.

Purity: 99.6% (based on high speed liquid chromatography)

| Elementary analysis ($C_{29}H_{30}N_2O_2$) | | | |
|---|---|---|---|
| | C | H | N |
| Calculated (%) | 79.45 | 6.85 | 6.39 |

-continued

| Elementary analysis ($C_{29}H_{30}N_2O_2$) | | | |
|---|---|---|---|
| | C | H | N |
| Found (%) | 79.67 | 6.84 | 6.19 |

IR(KBr.cm$^{-1}$): 1225 (ether linkage), 3470 and 3390 (ammonium group)

EXAMPLE 19

A 1 l glass reaction vessel was charged with 60.5 grams (0.25 mol) of 2-(4-hydroxy-3-methylphenyl)-2-(4-hydroxyphenyl)propane, 100.9 grams (0.6 mol) of m-dinitrobenzene, 82.8 grams of potassium carbonate and 650 ml of N,N-dimethylformamide. The mixture was reacted at 140–150° C. for 12 hours, cooled after ending the reaction, and poured into 3 l of water. Pale brown crystals obtained were 109 grams (90.0% yield) of crude 2-]3-methyl-4-(3-nitrophenoxy)phenyl]-2-[4-(3-nitrophenoxy)phenyl]propane having a melting point of 114–116° C.

In the second step, a 1 l glass reaction vessel was charged with above obtained pale brown crystals, 12 grams of active carbon, 1.2 grams of ferric chloride hexahydrate and 600 ml of IPA and stirred for 30 minutes under refluxing. Then 50 grams (1.0 mol) of hydrazine hydrate was dropped at 70–80° C. during 2 hours, and refluxed for further 6 hours with stirring. The resultant mixture was cooled, filtered to remove the catalyst, and ethyleneglycol monomethylether was distilled off. The residue was mixed with 500 ml of 10% aqueous methanol solution and 62.6 grams of concentrated hydrochloric acid, dissolved by warming, followed by adding 45 grams of sodium chloride, and cooled to 20–25° C. with stirring.

The separated crystals were filtered, neutralized with aqueous ammonia in toluene under stirring, and dissolved by warming to remove separated water layer.

n-Heptane was added to the solution. The separated crystals were filtered and dried to obtain 74.8 grams (70.5% yield) of 2-[3-methyl-4-(3-aminophenoxy)phenyl]-2-[4-(3-aminophenoxy)phenyl]-propane as pale brown crystals having a melting point of 114–116° C. The analytical results were as follows.

Purity: 99.3% (based on high speed liquid chromatography)

| Elementary analysis ($C_{28}H_{28}N_2O_2$) | | | |
|---|---|---|---|
| | C | H | N |
| Calculated (%) | 79.25 | 6.60 | 6.60 |
| Found (%) | 79.65 | 6.61 | 6.14 |

IR(KBr.cm$^{-1}$): 1225 (ether linkage), 33440 and 3360 (ammonium group)

EXAMPLE 20

A 1 l glass reaction vessel was charged with 64 grams (0.25 mol) of 2-(4-hydroxy-3,5-dimethylphenyl)-2-(4-hydroxyphenyl)propane, 100.9 grams (0.6 mol) of m-dinitrobenzene, 82.8 grams of potassium carbonate and 630 ml of N,N-dimethylformamide. The mixture was reacted at 140–150° C. for 14 hours, cooled after ending the reaction, and poured into 3,000 ml of water. The pale brown crystals obtained were 106 grams (85.0% yield) of crude 2-[3,5-dimethyle-4-(3-nitrophenoxy)-phenyl]-2-[4-(3-nitrophenoxy)phenyl]propane having a melting point of 137–139° C.

In the next step, a 1 l glass vessel was charged with above obtained pale brown crystals, 12 grams of active carbon, 1.2 grams of ferric chloride hexahydrate and 630 ml of ethyleneglycol monomethylether, and refluxed for 30 minutes with stirring. Then 50 grams (1.0 mol) of hydrazine hydrate was dropped during 2 hours, stirred for further 8 hours under refluxing, cooled, filtered to remove the catalyst, and ethyleneglycol monomethylether was distilled off. The residue was mixed with 500 ml of 25% aqueous methanol solution and 62.5 grams of concentrated hydrochloric acid, dissolved by warming, followed by further adding 50 grams of sodium chloride and cooled to 20–25° C. with stirring. The separated crystals were filtered, mixed with 400 ml of 25% aqueous methanol solution, dissolved by warming, followed by adding 40 grams of sodium chloride, and cooled to 20–25° C. with stirring. The separated crystals were filtered, neutralized in water with aqueous ammonia, filtered again, and washed with water. The crystals thus obtained was dissolved in toluene by warming and separated water layer was removed. n-Heptane was added to the solution. The separated crystals were filtered and dried. The pale brown crystals obtained were 82.1 grams (75% yield) of 2-[3,5-dimethyl-4-(3-aminophenoxy)phenyl]-2-[4-(3-aminophenoxy)-phenyl]-propane having a melting point of 137–139° C. Results of analysis were as follows.

Purity: 99.2% (based on high speed liquid chromatography)

| Elementary analysis ($C_{29}H_{30}N_2O_2$) | | | |
|---|---|---|---|
| | C | H | N |
| Calculated (%) | 79.45 | 6.85 | 6.39 |
| Found (%) | 79.65 | 6.62 | 5.98 |

IR(KBr.cm$^{-1}$): 1230 (ether linkage), 3450 and 3370 (ammonium group)

What we claim is:

1. Method for preparing a bis(3-aminophenoxy) derivative of aromatic or bridged aromatic hydrocarbon represented by the following general formula:

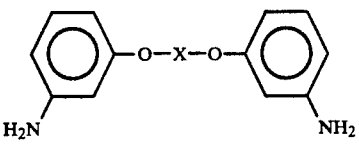

where X is

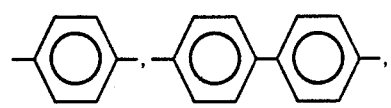

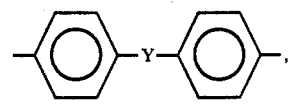

-continued

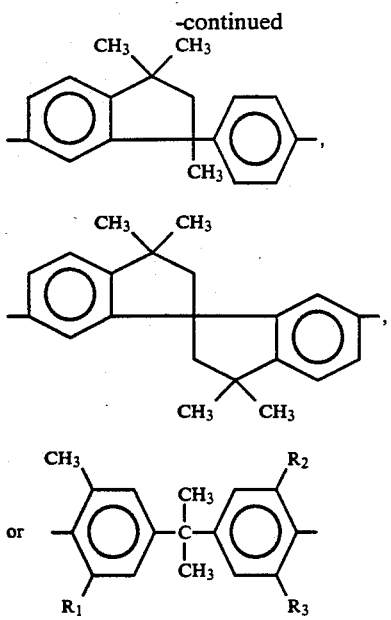

where Y is hydrocarbons of $C_1$-$C_{10}$, —C(CF$_3$)$_2$—, —CO—, —S—, —SO—, —SO$_2$—, or —O—, and $R_1$, $R_2$, and $R_3$ each independently are H, or CH$_3$, which comprises conducting a condensation reaction of m-dinitrobenzene in a dipolar aprotic solvent in the presence of a base at a temperature of 110° to 240° C. with a dihydroxy derivative of aromatic or bridged aromatic hydrocarbon represented by the following general formula:

HO—X—OH where X is the same as above,
and reducing the resultant bis(3-nitrophenoxy) derivative of aromatic or bridged aromatic hydrocarbon represented by the following general formula (II):

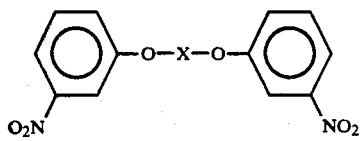

where X is the same as above.

2. The method of claim 1 wherein said condensation reaction is conducted in the presence of a nitrogen containing aliphatic polyether represented by the following general formula:

N[—CH$_2$—CH$_2$—O(—CH$_2$—CH$_2$—O)$_n$—R]$_3$ where R is $C_1$-$C_4$ alkyl and n is an integer of 1 or 2, as a reaction accelerator.

3. The method of claim 1 wherein said base is carbonate or hydrogen carbonate of alkali metal.

4. The method of claim 1 wherein said reducing reaction is conducted with hydrazine.

5. The method of claim 1 wherein said reducing reaction is conducted with hydrogen in the presence of a catalyst.

6. The method of claim 1 wherein said dihydroxy derivative is represented by the following general formula:

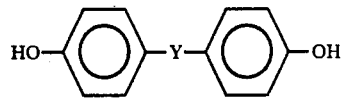

where Y is hydrocarbons of $C_1$-$C_{10}$, —C(CF$_3$)$_2$—, —CO—, —S—, —SO—, —SO$_2$—, or —O—.

7. The method of claim 1 wherein said dihydroxy derivative is hydroquinone.

8. The method of claim 1 wherein said dihydroxy derivative is 4,4'-dihydroxybiphenyl.

9. The method of claim 1 wherein said dihydroxy derivative is 1-(4-hydroxyphenyl)-1,3,3-trimethyl-6-hydroxyindan.

10. The method of claim 1 wherein said dihydroxy derivative is 6,6'-dihydroxy-3,3,3',3'-tetramethyl-1,1'-spirobiindan.

11. The method of claim 1 wherein said dihydroxy derivative is a 2,2-bis(4-hydroxyphenyl)propane derivative represented by the following general formula:

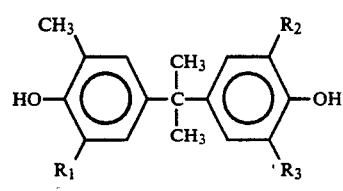

where $R_1$, $R_2$ and $R_3$ are each independently H, or CH$_3$.

12. The method of claim 1 wherein the yield of the bis(3-aminophenoxy)-derivative is at least about eighty percent by weight.

13. A method for preparing a bis(3-nitrophenoxy)-derivative represented by the following general formula:

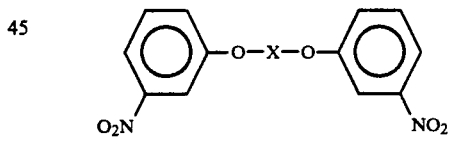

where X is

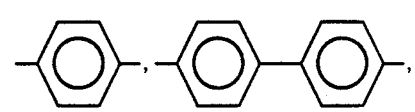

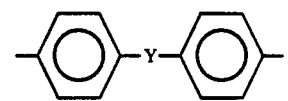

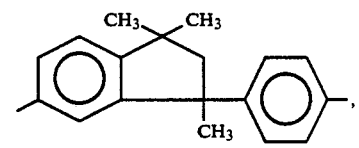

-continued

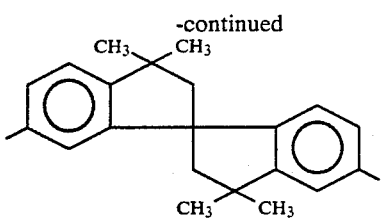

or

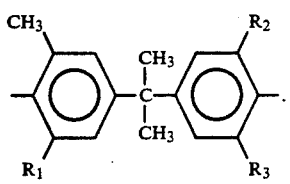

where Y is hydrocarbons of $C_1$-$C_{10}$, —C(CF$_3$)$_2$—, —CO—, —S—, —SO—, —SO$_2$—, or —O—, and $R_1$, $R_2$, $R_3$ are H, or CH$_3$, which comprises conducting a condensation reaction of m-dinitrobenzene in a dipolar aprotic solvent in the presence of a base with a dihydroxy derivative represented by the following general formula:

$$HO-X-OH$$

where X is the same as above, under conditions whereby said bis(3-nitrophenoxy)-derivative is prepared.

14. The method of claim 13 wherein said bis(3-nitrophenoxy)-derivative is prepared in a yield of at least about ninety percent by weight.

15. The method of claim 1 wherein the condensation reaction is conducted in the absence of a reaction accelerator.

* * * * *